United States Patent [19]

Seth

[11] Patent Number: 4,867,987
[45] Date of Patent: Sep. 19, 1989

[54] PHARMACEUTICAL PRODUCT FOR THE SUSTAINED RELEASE OF IBUPROFEN

[75] Inventor: Pyare L. Seth, Aesch, Switzerland

[73] Assignee: Mepha AG, Aesch, Switzerland

[21] Appl. No.: 944,552

[22] Filed: Dec. 19, 1986

[30] Foreign Application Priority Data

Jun. 25, 1986 [CH] Switzerland .......................... 2553/86

[51] Int. Cl.$^4$ .......................... A61K 9/36; A61K 9/58; B01J 13/02
[52] U.S. Cl. .................................... 424/480; 424/465; 424/481; 424/482; 427/213.31; 514/963
[58] Field of Search .................... 427/213.31; 424/465, 424/469, 482, 480, 481; 514/963

[56] References Cited

U.S. PATENT DOCUMENTS

| | | | |
|---|---|---|---|
| 3,371,015 | 2/1968 | Sjogren et al. | 424/482 X |
| 4,092,350 | 5/1978 | Miura et al. | 514/870 X |
| 4,447,454 | 5/1984 | Lednicer | 514/647 |
| 4,522,826 | 6/1985 | Sunshine et al. | 514/563 |
| 4,555,524 | 11/1985 | Gruber et al. | 514/570 |
| 4,585,783 | 4/1986 | Sunshine et al. | 514/408 |
| 4,587,249 | 5/1986 | Sunshine et al. | 514/265 |
| 4,606,909 | 8/1986 | Bechgaard et al. | 424/482 X |
| 4,666,705 | 5/1987 | DeCrosta et al. | 424/482 |
| 4,684,516 | 8/1987 | Bhutani | 424/469 |

FOREIGN PATENT DOCUMENTS

| | | |
|---|---|---|
| 903540 | 2/1986 | Belgium . |
| 61217 | 9/1982 | European Pat. Off. . |
| 2908794 | 9/1979 | Fed. Rep. of Germany . |
| 56-30402A | 2/1981 | Japan . |
| 59-122425A | 7/1984 | Japan . |
| WO84/00488 | 2/1984 | World Int. Prop. O. . |
| WO84/00490 | 2/1984 | World Int. Prop. O. . |
| WO85/02540 | 6/1985 | World Int. Prop. O. . |
| WO85/02542 | 6/1985 | World Int. Prop. O. . |

OTHER PUBLICATIONS

Summary of Pre-Examination Search Report.
Computer Printouts from Am. Chemical Society and Derwent Publications.
Datasheets in respect of Chemical Abstracts, WPI and WPIL.
Eudragit ®E. Eudragit ®E. 30 D, Anwendungstechnisches Merkblatt, Info ED-11/e, Röhm Pharma GmbH, Darmstadt, May 1980.
Eudragit TM L/S, Eudragit TM L/S, Technical Application Pamphlet, Info L/S-12/e, Röhm Pharma GmbH, Weiterstadt, Mar. 1979.
Eudragit ®L. Eudragit ®L30D, Anwendungstecnisches Merkblatt, Info LD-11/e, Röhm Pharma GmbH, Weiterstadt, May 1980.
Pharmacopeial Forum, vol. 14, No. 5, Sep.-Oct. 1988, "In Process Revision" pp. 4403–4405.
Roche Lexikon Medizin, Urban & Schwarzenberg, München-Wien-Baltimore, 1984, pp. 386, 387, 1014 & 1015.
Pharmaceutical Dosage Forms, Ed. by H. A. Lieberman et al., Marcel Dekker Inc., New York, 1980, vol. 1, pp. 72, 83, 84, 134 and 135.
Ullmann's Encyclopedia of Industrial Chemistry, 5th Ed., VCH Verlagsgesellschaft mbH, Weinheim, 1987 FRG, vol. A8, pp. 315, 316 and 345.
Merck Index pp. 601 and 1092 (1983).

Primary Examiner—Richard D. Lovering
Attorney, Agent, or Firm—Wenderoth, Lind & Ponack

[57] ABSTRACT

The product consists of tablets which contain at least 600 mg of ibuprofen and a binder, or a mixture of binders, based on cellulose and cellulose derivatives in the form of microspheres which are coated with an acrylic resin of defined nature and are compressed together with a disintegrant; the tablets are preferably also coated with a lacquer layer. As a consequence of the high content of active compound and its delayed release in the body, the therapeutic treatment with ibuprofen can be reduced to a minimum number of intakes and dose units per day.

10 Claims, No Drawings

PHARMACEUTICAL PRODUCT FOR THE SUSTAINED RELEASE OF IBUPROFEN

The active compound 2-(4-isobutylphenyl)propionic acid, which is known under the name ibuprofen, is, because of the good analgesic and antiinflammatory properties, widely used for the treatment of states of mild to moderate pain, for non-articular rheumatism and for inflammatory and degenerative joint disorders. Compared with other non-steroidal antiinflammatory products, ibuprofen is distinguished by, inter alia, being well tolerated by the stomach.

The recommended dose for the treatment of, in particular, rheumatoid arthritis and osteoarthritis is 900 to 1600 mg/day (L.S. Goodman and A. Gilman, The Pharmacological Basis of Therapeutics, 5th Edition, MacMillan Publ. Co., N.Y., 1975, page 343). According to Arzneimittel-Profile/Basisinformation uber arzneiliche Wirkstoffe (Drug profile/basic information on medicinal active compounds) [Govi-Verlag GmbH and Pharamzeutischer Verlag, Frankfurt a/Main (FRG), 2nd supplement, November 1983, Ibuprofen] the daily dose is 1200 to 1600 mg; it may in isolated cases be increased to 2,400 mg/day, but should not be increased above this.

A dose as high as this can be used without misgivings because the active compound is rapidly and completely excreted from the body: it is to be relied on that ibuprofen and its metabolites have been completely eliminated 24 hours after the last administration (Arzneimittel-Profile, ibidem).

There is, to be sure, another side to this rapid elimination. In order to ensure an effective concentration of active compound in the body, and specifically in the plasma, throughout the day, the administration of ibuprofen must be repeated every few hours. The dosage regimen for adults is, for example, 1 to $2\times200$ mg tablets three times a day, $1\times400$ mg tablet three or four times a day, or 400 mg every four to six hours.

With this frequency of intake, the patient may in time become exasperated with or antipathetic to the medicament and make the treatment unsuccessful. In addition, the frequent intake of amounts of active compound which again and again exceed definitely the effective blood level raises a risk of side effects, especially in the gastro-intestinal tract.

For this reason, it would be desirable to have available a pharmaceutical form which contains a dose higher than about 300 or 400 mg of active compound and which would release the contents over a longer period of time. It would be possible in this way to reduce the frequency of intake and the number of dose units per day, and simultaneously also be almost suppress the fluctuations of the blood level, which hitherto were unavoidable, between a very high and a very low concentration of ibuprofen (fluctuating index).

There have been, in fact, many suggestions in the above mentioned sense. Thus, in DE No. 2,908,794 and JP No. 81-30,402 A, solid preparation for the sustained release of ibuprofen and other physiologically active compounds are described; in said preparations, the active compound is embedded in a polymer matrix which dissolves in the gastric juice or only in the intestinal juice. They are obtained by polymerizing by means of irradiation, suitably with γ-rays, an aqueous dispersion of the active compound and one or more vitrifiable monomers like ethylene glycol dimethacrylate or triethylene glycol dimethacrylate, at a temperature below 0° C., preferably between −20° and −80° C. The preparations are obtained as microspheres or hard films.

According to BE No. 903,540 powders with sustained release are prepared from active compounds of any kind and any type of activity, inter alia from ibuprofen as well as from saccharin, aspartam and the like. To this aim, the solvents or dispersing agents are removed from a solution or a dispersion of the active compound in a non toxic polymer, for instance cellulose derivatives, polyacrylic acid and polymethacrylic acid derivatives, polyvinyl compounds, polysiloxanes, polyurethanes and so on; there are obtained in this way microspheres.

The above mentioned processes, however, apparently have been up to now missing an application in the techniques. This failure should be ascribed first to the considerable expenditure of apparatuses and the difficulties which are involved in including and controlling a polymerization at temperatures of from −20° to −80° C., or in removing a solvent from a solution up to the slightest traces. Above all, indeed, it is in practice impossible to produce in accordance with these processes solid preparations with a high content of ibuprofen.

Nevertheless, controlled-release products have also appeared, such as, inter alia, the products Dolgit® retard or Novogent® N (Rote Liste, Editio Cantor, Aulendorf/FRG 1984), in which the ibuprofen is in the form of capsules containing 400 and 300 mg respectively. Normally two of these capsules are administered twice a day; the total daily dose may be as much as six capsules. Furthermore, European Patent Application No. 61,217 describes a product with delayed release of the active compound, which is composed of hard gelatin capsules containing 300 mg of ibuprofen. As a posology, taking two capsules two times a day, every 12 hours, it recommended. The production is carried out in a coating pan. Ibuprofen in the form of a powder is bound, by means of low-viscosity polyvinylpyrrolidone, over a spherical core composed of sugar and starch, the spheroids are then coated with a high-viscosity polyvinylpyrrolidone and the final spheroids are encapsulated.

As is generally known, the biggest capsules which are available on the market - standard size 0 to 00 - have in respect of spheroids or pellets a capacity which corresponds at the most to 350 mg of active compound. For this reason, the above mentioned scheme of treatment is necessary, although it does by no means fulfill the requirements as put at the beginning. Moreover, the process of preparation causes a considerable expenditure of work for coating and evaporating the solvent in time-consuming and repeated operations.

Although these products have the required controlled-release action, they do not achieve the objective to the extent that the level of the dose unit (300 or 400 mg), which is the same as in the conventional tablets, does not allow the desired reduction in intakes.

On the other hand, attempts to prepare controlled-release products containing, for example 600 to 800 mg of active compound have failed. In fact, ibuprofen has a low melting point (75°-77° C.) which is reduced further on mixing with customary excipients. As a consequence, the pressure during tabletting is sufficient partially to melt the active compound. This makes the solid composition sticky, which considerably impedes the preparation of tablets. These circumstances have a particularly disadvantageous effect in the preparation of controlled-release products which frequently contain fatty compositions or similar lowmelting auxiliaries like lipids such as hydrogenated oils or paraffins according to JP No. 84-122,425 A.

Thus, despite all attempts it has not hitherto been possible to provide a pharmaceutical form of ibuprofen which, due to a high content of active compound and delayed release in the body, allowed only one unit to be administered twice a day.

A pharmaceutical product which contains ibuprofen in a surprisingly high, to date inconceivable, dose and regularly releases the active compound in the body over a longer period of time has now been found, so that the requirements which were set long ago have finally been met.

The product is in the form of tablets which contain the active compound in microspheres, disintegrate fast in an aqueous medium, and have the following composition:

(a) ibuprofen in an amount of at least 600 mg and
(b) a binder, or a mixture of binders, based on cellulose
and cellulose derivatives, both of which are in the form of a homogeneous mixture and in the form of microspheres, which, in turn, are coated with a layer of
(c) an acrylic resin of neutral character and average molecular weight of around 800,000, composed of copolymers
of acrylic and methacrylic esters of the partial formula:

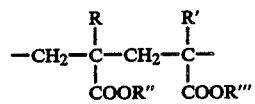

in which each of R and R' denotes hydrogen or methyl, and each of R" and R'" denotes methyl or ethyl, or of an acrylic resin of similar behavior, and the coated microspheres are homogeneously mixed with (d) a disintegrant, or a mixture of disintegrants, and are compressed to form tablets.

The tablets according to the invention are obtained by mixing together the ibuprofen and the binder, or the mixture of binders, based on cellulose derivatives to give a homogeneous mixture and moistening with water, shaping the mixture into microspheres by extrusion, drying the microspheres, coating with an aqueous dispersion of an acrylic resin as above defined, and drying, mixing the coated microspheres with the disintegrant, or the mixture of disintegrants, to give a homogeneous mixture, and compressing the mixture to form tablets.

In a preferred embodiment the tablets are coated with a lacquer layer.

Particularly suitable binders are cellulose and water-soluble cellulose derivatives such as methylcellulose, ethylcellulose, carboxymethylcellulose (also called cellulose glycolate), hydroxyethylcellulose, hydroxypropylcellulose and celluloseethanesulfonic acid. In this context, see also Ullmanns Encyklopädie der technischen Chemie (Ullmann's encyclopedia of industrial chemistry), 4th edition, volume 9 pages 192-212, Verlag Chemie GmbH, Weinheim (FRG) 1975.

Among the many acrylic resins of the abovementioned nature, that which is commercially available under the tradename Eudragit E 30 D (Rohm Pharma GmbH, Darmstadt, FRG) has proved very particularly appropriate for the purposes of the invention.

Disintegrants which can be used are, inter alia, a polyvinylpyrrolidone, starch, a starch ether, carboxymethylstarch (also called starch glycolate), a pectin and other customary swelling agents such as cellulose etc.

The tablet according to the invention can contain amounts of ibuprofen as high as, for example, 600 to 1200 mg, or even more. Indeed, this amount does not depend, for instance, upon the volume which a patient at the most can be expected to swallow and just a little upon the capacity of a commercial capsule, but only upon the form and dimensions of the punch of the table press.

Examples
Tablets of the following composition are prepared:

| | | | Example 1 | Example 2 | Example 3 |
|---|---|---|---|---|---|
| | | Ibuprofen | 800.0 mg | 800.0 mg | 600.0 mg |
| A | { | Microcrystalline cellulose Avicel ® PH 102 | (1) 130.0 " | 133.3 " | 100.0 " |
| | | Microcrystalline cellulose with 8% carboxymethylcellulose Avicel ® RC 581 | (1) 130.0 " | 133.3 " | 100.0 " |
| | | Hydroxypropylcellulose Pharmcoat ® 603 | (2) 40.0 " | 40.0 " | 30.0 " |
| | | Acrylic resin Eudragit ® E 30 D | (3) 53.0 " | 53.3 " | 40.0 " |
| | | Highly disperse silica Aerosil ® 200 | (4) 15.0 mg | 13.0 mg | 10.0 mg |
| | | Magnesium stearate | 12.0 " | 12.0 " | 9.0 " |
| | | Talc | 30.0 " | 60.0 " | 45.0 " |
| B | { | Crosslinked, insoluble homopolymers of N—vinyl-2-pyrrolidone Crospovidone NF Polyplasdone ® XL 10 | (5) 50.0 " | — | — |
| | | Sodium salt of a carboxymethyl starch of a low degree of substitution US Pharmacopoeia XXI Explotab ®, Primojel ® | (6) 10.0 " | 60.0 " | 45.0 " |

-continued

Examples
Tablets of the following composition are prepared:

|  | Example 1 | Example 2 | Example 3 |
|---|---|---|---|
|  | 1270 mg | 1305 mg | 979 mg |

(1) Manufacturer: FMC Corporation, Chicago (IL, USA)
(2) Manufacturer: Shin-Etsu Chemical Co., Cellulose Div., Tokyo (Japan)
(3) Manufacturer: Rohm Pharma GmbH, Darmstadt (FRG)
(4) Manufacturer: Degussa AG, Frankfurt a/Main (FRG)
(5) Manufacturer: GAF Corporation, Wayne (NJ, USA)
(6) Manufacturer: AVEBE International Marketing and Sales, Foxhol (The Netherlands)

The substances designated A are mixed together, moistening with water or an aqueous solution of the binders, and the moist mixture is shaped into microspheres through an extruder and a spheronizer (roundingoff machine), which are then dried in a stream of air at about 45° C. The dried microspheres are coated with an aqueous suspension of the indicated acrylic resin in a fluidized-bed process at a temperature of about 30° C. After this, the coated microspheres are mixed, in a mixing apparatus, with the substances listed under B, and the resulting mixture is compressed to form tablets. The tablets are preferably then coated with a lacquer layer in a coating pan.

The rate of dissolution in water of the tablets prepared as in Examples 1, 2 and 3 was determined by the following method:

procedure: U.S. Pharmacopoeia XXI, page 1243 (1985)

apparatus: apparatus 1, with basket rotating at 150 rpm medium: aqueous phosphate buffer, pH 6.5 volume: 900 ml volume of the sample: 1 ml times of sampling: after 30, 60, 120, 180, 240, 300, 360 and 420 minutes measurement: spectroscopically at 221 nm UV.

The results show that the following proportionate amounts (means) of ibuprofen are released from the tablets over the course of time.

|  | Example 1 | Examples 2 and 3 |
|---|---|---|
| after 1 hour | 21.6% | 27.6% |
| after 2 hours | 37.8% | 42.8% |
| after 4 hours | 61.9% | 64.4% |
| after 7 hours | 80.5% | 76.8% |
| after 10 hours | 99.7% | 94.0% |

In other words, in an aqueous medium the active compound is virtually quantitatively released from the tablets according to the invention within about 10 hours. Furthermore, it is obvious from the chronological course of the release that the tablets disintegrate fast and that the release is progressing regularly. For these reasons, an effective and sustained blood level can arise in the body already shortly after the intake, as has been established in the clinical trials.

In order to test the efficacy of the product, its bioavailability was determined in two separate in vivo tests and compared with that of other pharmaceutical formulations of ibuprofen. The said in vivo tests were carried out in August, September and October and in November and December 1984 by IPHAR, Institut fur Klinische Pharmakologie GmbH, Höhenkirchen (FRG) on five and eight, respectively, healthy male volunteers.

The following controlled-release products were used for comparison in the first in vivo test:

(A) Novogent® N, 300 mg capsules Manufacturer: Temmler-Werke, Vereinigte Chemische Fabriken, Marburg (FRG)

(B) Dolgit® retard, 400 mg capsules Manufacturer: Dolorgiet Arzneimittelfabrik Peter Doll KG, Bonn (FRG)

(C) MP 031, 600 mg lacquered tablets as in Example 3 (according to the invention) and a product with no delayed action, namely:

(D) Brufen®, 400 mg coated tablets Manufacturer: Adolf Klinge u. Co., Munich (FRG).

Each subject received, in each case at an interval of one week, a single oral dose of 400 mg Dolgit retard (B) or Brufen (D) and 500 mg Novogent N (2×300 mg capsules, A) or one 600 mg MP 031 Lacquered tablet (C).

The second in vivo test compared the following controlled-release products:

MP 031, 600 mg lacquered tablets as in Example 3 (according to the invention)

MP 031', 800 mg lacquered tablets as in Example 1 (according to the invention)

Fenbid® retard, 300 mg capsules

Manufacturer: Smith, Kline and French Laboratories Ltd., Welwyn Garden City (Hertfordshire, England) and the above mentioned product with no delayed action Brufen®, 400 mg coated tablets Manufacturer: Adolf Klinge u. Co., Munich (FRG).

Each of the eight subjects received, in each case at an interval of one week, a single oral dose of 600 mg MP 031, 800 mg MP 031', 600 mg Fenbid retard (2×300 mg capsules) or 800 mg Brufen (2×400 mg coated tablets).

Blood samples were taken from each subject in accordance with a set schedule, and the plasma obtained from them was analyzed for the concentration of ibuprofen. The determination was based on the method of S. F. Lockwood and J. C. Wagner [Journal of Chromatography 232 (1982), 335–343]by a high-pressure liquid chromatography procedure.

The parameters listed in the following tablets were calculated from the concentrations of ibuprofen measured in the plasma at various times:

the maximum concentration, $C_{max}$ the time until the maximum concentration was reached, $t_{max}$ the area under the concentration curve, AUC the means retention time, MRT, and the elimination half-life, $t_{1/2}$.

TABLE 1

| Para-meter | | Subject 1 | 2 | 3 | 4 | 5 | X | SD |
|---|---|---|---|---|---|---|---|---|
| A | Cmax | 5.30 | 15.17 | 13.36 | 9.73 | 13.95 | 11.95 | 4.49 |
|   | tmax | 2.5 | 6.0 | 2.5 | 3.0 | 2.5 | 3.4 | 1.8 |
|   | AUC | 56.38 | 134.23 | 140.36 | 93.15 | 127.70 | 114.67 | 39.20 |
|   | MRT | 8.82 | 8.16 | 10.60 | 9.65 | 9.83 | 9.35 | 1.08 |
|   | $t_{\frac{1}{2}}$ | 8.36 | 5.77 | 6.27 | 5.11 | 5.35 | 6.44 | 1.34 |
| B | Cmax | 10.86 | 16.14 | 17.07 | 10.42 | 7.06 | 12.78 | 4.69 |
|   | tmax | 4.0 | 4.0 | 2.5 | 2.5 | 12.0 | 5.6 | 4.3 |
|   | AUC | 66.00 | 108.35 | 133.49 | 65.81 | 115.04 | 105.72 | 28.53 |
|   | MRT | 6.07 | 5.61 | 6.94 | 5.37 | 14.14 | 8.19 | 4.00 |
|   | $t_{\frac{1}{2}}$ | 2.21 | 2.30 | 3.65 | 2.96 | | 2.72 | 0.81 |
| C | Cmax | 3.71 | 23.11 | 25.92 | — | 12.25 | 16.25 | 10.23 |
|   | tmax | 4.0 | 4.0 | 3.0 | — | 4.0 | 3.8 | 0.5 |
|   | AUC | 27.05 | 142.24 | 198.84 | — | 157.46 | 131.40 | 73.56 |
|   | MRT | 6.79 | 6.31 | 7.53 | — | 10.89 | 7.88 | 2.07 |
|   | $t_{\frac{1}{2}}$ | 3.52 | 2.45 | 4.48 | — | 3.56 | 3.50 | 0.83 |
| D | Cmax | 4.34 | 37.05 | 37.89 | 27.33 | 12.07 | 22.84 | 17.19 |
|   | tmax | 1.5 | 0.8 | 1.5 | 1.5 | 8.0 | 2.9 | 3.4 |
|   | AUC | 13.54 | 92.47 | 140.07 | 76.47 | 131.22 | 94.32 | 57.69 |
|   | MRT | 2.69 | 2.43 | 4.04 | 3.21 | 9.11 | 4.57 | 3.11 |
|   | $t_{\frac{1}{2}}$ | 1.65 | 1.57 | 2.11 | 1.64 | 3.99 | 2.33 | 1.13 |

Pharmacokinetic parameters of ibuprofen determined in five healthy subjects after oral administration of Novogent N (A, 600 mg), Dolgit retard (B, 400 mg), MP 031 (C, 600 mg) and Brufen (D, 400 mg).
$C_{max}$ = maximum plasma concentration ($\mu g \cdot ml^{-1}$)
$t_{max}$ = time until maximum plasma concentration is reached (h)
AUC = area under the curve of plasma levels ($\mu g \cdot ml^{-1} \cdot h$)
MRT = mean retention time (h)
$t_{\frac{1}{2}}$ = elimination half-life (h)
X = mean
SD = standard deviation.

TABLE 2

| | Parameter | Subject 1 | 2 | 3 | 4 | 5 | 6 | 7 | 8 | X | SD |
|---|---|---|---|---|---|---|---|---|---|---|---|
| MP 031 | Cmax | 14.41 | 16.08 | 27.21 | 27.25 | 17.40 | 7.33 | 19.14 | 15.63 | 18.06 | 6.63 |
|   | tmax | 2.5 | 4.0 | 5.0 | 2.5 | 6.0 | 6.0 | 3.0 | 6.0 | 4.4 | 1.6 |
|   | AUC | 160.62 | 207.48 | 239.78 | 175.46 | 170.49 | 121.29 | 127.56 | 162.66 | 170.67 | 38.94 |
|   | MRT | 10.69 | 9.71 | 8.59 | 7.03 | 8.42 | 10.01 | 6.42 | 9.30 | 8.77 | 1.47 |
| MP 031' | Cmax | 11.60 | 14.51 | 27.60 | 25.20 | 17.02 | 15.18 | 21.36 | 19.54 | 19.00 | 5.50 |
|   | tmax | 2.5 | 7.0 | 5.0 | 6.0 | 4.0 | 6.0 | 6.0 | 3.0 | 4.9 | 1.6 |
|   | AUC | 196.71 | 225.73 | 271.31 | 245.60 | 201.03 | 179.65 | 189.37 | 195.70 | 213.14 | 31.63 |
|   | MRT | 12.06 | 10.93 | 8.85 | 8.84 | 9.28 | 10.69 | 8.44 | 9.11 | 9.77 | 1.29 |
| FENBID | Cmax | 14.78 | 13.36 | 22.11 | 21.72 | 13.39 | 25.69 | 14.85 | 17.52 | 17.93 | 4.68 |
|   | tmax | 5.0 | 4.0 | 3.0 | 5.0 | 3.0 | 2.5 | 2.5 | 3.0 | 3.5 | 1.0 |
|   | AUC | 169.79 | 175.44 | 212.87 | 159.97 | 137.36 | 154.15 | 124.21 | 152.35 | 160.77 | 26.76 |
|   | MRT | 10.92 | 9.55 | 8.68 | 6.01 | 7.34 | 6.28 | 7.14 | 7.22 | 7.89 | 1.69 |
| BRUFEN | Cmax | 49.01 | 59.29 | 90.39 | 54.57 | 56.37 | 49.11 | 27.12 | 55.36 | 55.15 | 17.41 |
|   | tmax | 1.0 | 1.5 | 2.0 | 2.5 | 0.5 | 2.5 | 1.0 | 1.5 | 1.6 | 0.7 |
|   | AUC | 318.04 | 285.44 | 377.91 | 214.23 | 249.14 | 178.93 | 179.21 | 262.60 | 258.19 | 68.88 |
|   | MRT | 6.00 | 6.02 | 5.92 | 7.97 | 3.77 | 7.61 | 6.16 | 4.86 | 6.04 | 1.35 |
|   | $t_{\frac{1}{2}}$ | 4.1 | 2.5 | 2.8 | 2.9 | 1.6 | 2.5 | 4.1 | 1.8 | 2.8 | 0.9 |

Pharmacokinetic parameters of ibuprofen determined in eight healthy subjects after oral administration of MP 031 (600 mg), MP 031' (800 mg), Fenbid retard (600 mg) and Brufen (800 mg)
$C_{max}$ = maximum plasma concentration ($\mu g \cdot ml^{-1}$)
$t_{max}$ = time until maximum plasma concentration is reached (h)
AUC = area under the curve of plasma levels ($\mu g \cdot ml^{-1} \cdot h$)
MRT = mean retention time (h)
$t_{\frac{1}{2}}$ = elimination half-life (h)
X = mean
SD = standard deviation.

There were marked differences between the time curves of the plasma concentrations of the individual pharmaceutical forms administered. Brufen (D) had the highest maximum plasma concentration $C_{max}$ and the shortest time until the maximum concentration was reached $t_{max}$, and the means retention time MRT and the half-life $t_{1/2}$ were lowest, as was expected for a non-controlled-release formulation.

The calculated areas under the concentration curves AUC represent the extent of the bioavailability of the individual formulations. It is evident from Table 1 that the bioavailability was greatest for product (C) according to the invention, with a AUC of 131.40, and there is no doubt that this derives from the combined effects of the higher content of active compound and its delayed release. According to Table 2, among the controlled-release formulations the products MP 031 and MP 031' according to the invention likewise had the highest AUC, at 170.67 and 213.14 respectively, that is to say the greatest bioavailability.

However, the crucial advantage is that the invention provides a product which contains, in a unit dose with a longer duration of action, an amount of active compound which is at least two to three times higher than was hitherto possible. It was, however, fully unexpected that adding only 10 to 15% of external phase (i.e. the substances marked B, as a whole, in Examples 1, 2 and 3) to the microspheres would make possible the preparation of tablets which, although containing 600 mg of ibuprofen or even more, are of not too big, that is of acceptable (i.e. swallowable), dimensions and disintegrate in an aqueous medium as fast as any conventional tablet (that is, tablets which are produced by pressing a granulate or a powder).

The microspheres which are released in the stomach by the disintegration, continuously "flow" into the intestine in a manner which is to a large extent independent from the periodical evacuation of the stomach, and they display their delayed action over the whole passage duration. Thus, owing to the outstanding efficacy, which is evident from the bioavailability, medical science is provided with a product which permits successful treatment of the above-mentioned indications with minimal demands on the patients (number of intakes each day and number of dose units per intake or per day).

I claim:

1. A pharmaceutical product for the sustained release of ibuprofen in the body, in the form of tablets which contain the active compound in microspheres, disintegrate fast in an aqueous medium, and have the following composition:
   (a) ibuprofen in an amount of at least 600 mg and
   (b) a binder, or a mixture of binders, based on cellulose and cellulose derivatives, all of which are in the form of a homogenous mixture and in the form of microspheres which, in turn, are coated with a layer of (c) an acrylic resin of neutral character and average molecular weight of around 800,000, composed of copolymers of acrylic and methacrylic esters of the partial formula:

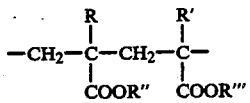

in which each of R and R' denotes hydrogen or methyl, and each of r" and R'" denotes methyl or ethyl, and the coated microspheres are homogeneously mixed with (d) a disintegrant, or a mixture of disintegrants in an amount which makes up only 10 to 15% of the whole weight, and the resulting homogenous mixture is compressed to form tablets.

2. The product as claimed in claim 1, wherein the tablets are coated with a lacquer layer.

3. The product as claimed in claim 1, which contains 600 to 1200 mg of ibuprofen per tablet.

4. The product as claimed in claim 1, wherein the binder contains microcrystalline cellulose and a water-soluble cellulose derivative.

5. The product as claimed in claim 1, wherein the acrylic resin is composed of Edragit ® E 30 D.

6. The product as claimed in claim 1, wherein the disintegrant is cellulose, starch, a starch ether, a pectin or a swelling agent of similar action.

7. A process for the preparation of the pharmaceutical product as claimed in claim 1, which comprises mixing together the ibuprofen and the binder, or the mixture of binders, based on cellulose and cellulose derivatives to give a homogeneous mixture and moistening with water, shaping the mixture into microspheres by extrusion, drying the microspheres, coating with an aqueous dispersion of an acrylic resin of neutral character and average molecular weight of around 800,000, composed of copolymers of acrylic and methacrylic esters of the part-formula:

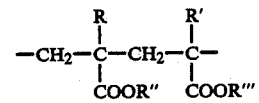

in which each of R and R' denotes hydrogen or methyl, and each of R" and R'" denotes methyl or ethyl, and drying, mixing the coated microspheres with the disintegrant, or the mixture of disintegrants, to give a homogeneous mixture, and compressing the mixture to form tablets.

8. The process as claimed in claim 7, wherein the resulting tablets are additionally coated with a lacquer layer.

9. The process as claimed in claim 7, wherein ibuprofen is used in an amount of 600 to 1200 mg per tablet.

10. The process as claimed in claim 7, wherein Eudragit ® E 30 D is used as acrylic resin.

* * * * *